United States Patent [19]

Bayense et al.

[11] Patent Number: 5,508,457
[45] Date of Patent: Apr. 16, 1996

[54] ESTERIFICATION PROCESS

[75] Inventors: Cornelis R. Bayense, Gameren, Netherlands; Hervé Hinnekens, Wetteren; Julien Martens, Lovendegem, both of Belgium

[73] Assignees: Engelhard De Meern B.V., Netherlands; Fina Research S.A., Belgium

[21] Appl. No.: 237,110

[22] Filed: May 3, 1994

[30] Foreign Application Priority Data

May 4, 1993 [EP] European Pat. Off. ............ 93201272
May 4, 1993 [EP] European Pat. Off. ............ 93201273

[51] Int. Cl.$^6$ ...................................................... C11C 3/00
[52] U.S. Cl. .................... 554/169; 554/30; 554/72; 554/77; 554/165; 554/167
[58] Field of Search .................... 554/72, 77, 30, 554/165, 167, 169

[56] References Cited

U.S. PATENT DOCUMENTS 4,032,550  6/1977  White et al. ............................ 554/167

FOREIGN PATENT DOCUMENTS

| 0372133 | 6/1990 | European Pat. Off. . |
| 92422375 | 11/1992 | European Pat. Off. . |
| 2295010 | 7/1976 | France . |
| 2510531 | 9/1975 | Germany . |
| 2710630 | 9/1978 | Germany . |
| 2092134 | 8/1982 | United Kingdom . |
| 2169895 | 7/1986 | United Kingdom . |

*Primary Examiner*—José G. Dees
*Assistant Examiner*—Deborah D. Carr
*Attorney, Agent, or Firm*—Weingarten, Schurgin, Gagnebin & Hayes

[57] ABSTRACT

The invention is directed to a process for the transesterification of carboxylic acid esters, in which process a catalyst is used which is substantially insoluble in the reaction mixture under reaction conditions, said catalyst comprising at least one silicate of the Group IVB elements of the Periodic Table as the active component.

14 Claims, No Drawings

ESTERIFICATION PROCESS

The present invention is directed to a process for the transesterification of carboxylic acid esters, using a heterogeneous catalyst.

The transesterification of carboxylic esters and derivatives thereof is a well-known method for preparing various commercially very interesting chemicals, such as glycerol and fatty acid esters, which can be used as intermediates for other important chemicals. A variety of processes is available therefor, all of which either use a homogeneous catalyst or a heterogeneous catalyst.

The transesterification of carboxylic acid esters comprises three groups of reactions, namely the transesterification with an alkanol, or alcoholysis, the transesterification with a carboxylic acid (or anhydride), the acidolysis, and the transesterification with a carboxylic acid ester. Of these reactions especially the alcoholysis of triglycerides is important.

In (trans)esterification reactions numerous homogeneous catalysts have been disclosed in the literature. Examples thereof are acids such as hydrochloric acid, sulfuric acid, p-toluene sulfonic acid and benzene sulfonic acid. Alkaline materials like alkali alkoxides and alkaline earth carbonates have also been disclosed. Another group of homogeneous catalysts that have been disclosed in the literature are based on the transition metal compounds with alkoxy or acyl groups, titanium chelates and titanium tin complexes.

The use of homogeneous catalysts of the types described hereinabove has various disadvantages. Both the acid and the alkaline materials lead to the formation of byproducts, and additionally it is required that the reaction product is neutralized at the end of the reaction. Presently a commercial catalyst for the methanolysis of triglycerides is sodiummethoxide, which has the disadvantage that the products become contaminated with sodium.

The alkaline catalysts, including those based upon the transition metals, are not resistant against the presence of water in the feed; they lead to unacceptable coloration of the product and they pose environmental problems.

U.S. Pat. No. 4,032,550 discloses an immobilized supported transition metal catalyst for direct esterification or ester-interchange. According to this patent generally titanium alkoxides have been used as precursor for the catalyst. However, those supported catalysts are not very easy to prepare in a reproducible manner and depending on the properties of the support they may lead to the production of unwanted byproducts.

It is an object of the present invention to provide a novel process for the transesterification of carboxylic acid esters, which process does not possess the disadvantages of the prior art processes.

The invention is based on the surprising insight, that certain silicates, namely the Group IVB silicates possess very good catalytic properties in the transesterification reactions. Accordingly, the present invention is directed to a process for the transesterification of carboxylic acid esters which process is based upon the use of a heterogeneous catalyst, said catalyst comprising a silicate of group IVB elements as the active component.

The said silicates can either be crystalline silicates or amorphous silicates. The active metal component used in the catalyst according to the invention is chosen from the group IVB of the Periodic Table of Elements. Said group IVB consists of the elements titanium, zirconium, hafnium and unnilquadium. Of those elements especially titanium and zirconium are preferred, whereby the best results are obtained with titanium.

Suitable catalysts are inter alia crystalline titanium silicate, crystalline titanium aluminium silicate, amorphous titanium silicate and the corresponding zirconium compounds. The crystalline titanium silicates can for example be the titanium molecular sieve zeolites, as disclosed in the U.S. Pat. Nos. 4,938,939; 4,853,202 and 5,011,591, and the titanium-aluminium silicates as disclosed in the European patent application No. 405,978 the contents of which publications is incorporated herein by way of reference. The amorphous silicates are generally based upon homogeneous mixed oxides of silicon and the said group IVB element. More in particular the homogeneous silicate is a mixed oxide of titanium and silicon.

One of the advantages of the present type of catalysts used in the invention lies therein, that the application of a fixed bed process has become possible, which has advantages over the slurry phase processes. Additionally other advantages of the invention are that no loss of catalyst occurs, no contaminations from the catalyst are present in the product, products of higher purity are obtained, such as glycerol, in alcoholysis reactions the free fatty acids present in the feed are also esterified during the process which is not the case with the commercially used $NaOCH_3$ catalyst and/or no or less foaming occurs. Another advantage of the invention lies in the reduced susceptibility of the catalyst for the composition of the feedstock, which allows the use of other, less purified feedstocks.

The process of the present invention can be carried out as a batch process, as a continuous process or a semicontinuous process. Depending on the process conditions and type of process chosen the catalyst can be slurried in the reaction mixture or can be used in a fixed bed.

The transesterification reaction according to the invention includes all types of transesterification of carboxylic acid esters with an alkanol, a carboxylic acid or an ester.

Examples of the reactions that can be carried out in the process of the present invention are the alcoholysis of triglycerides in slurry phase or fixed bed, that is the transesterification of triglyceride with an alkanol to the corresponding esters of the fatty acids; the production of dioctylphthalate, the production of polyvinylalcohol from polyvinyl acetate using an alkanol; and the transesterification of esters with carboxylic acids.

Of the reactions given hereinabove the transesterification of triglycerides, more in particular the methanolysis and the production of polyvinylalcohol are commercially very important reactions. In this respect it is remarked that the production of polyvinylalcohol from polyvinyl acetate is in fact a transesterification reaction of the acetate group with methanol, resulting in the formation of methylacetate and polyvinylalcohol.

Depending on the type of reaction used, the conditions can be and should be modified accordingly. Generally the reaction is carried out at increased temperature either at atmospheric pressure or under higher pressure. Preferably the reaction is carried out in a system only containing the reactants and the catalyst, although a solvent may be present, the solvent being inert to the reaction. Although the catalyst is not sensitive to the presence of water, it is to be remarked that water may react with one or more of the components, leading to a decreased yield in the process. The reaction is carried out at ambient temperature (20° C.) or higher temperatures, said temperature preferably being at least 45° C., more in particular between 45° and 300° C. The pressure at which the reaction is carried out will preferably be the autogeneous pressure when above atmospheric pressure, i.e. the pressure corresponding to the sum of the partial pressures of all components at the prevailing temperature. Generally the pressure will be between 1 and 50 bar.

The actual choice of the catalyst, that is crystalline or amorphous, type of active element and the actual structure of the silicate will depend on the type of reaction. As can be seen in the cited patent publications directed to the production of the crystalline molecular sieve silicates various pore sizes can be obtained. Depending on the size of the molecule, the diffusion characteristics thereof in the solvent used and the required reaction rate a specific pore size may be chosen. Suitable pore sizes of the various crystalline silicates range from 4 to 10 Å.

The titanium zeolites generally have the chemical composition $$(1+x/2)(1.0\pm0.25\ M_{2/n}O):TiO_2:xAlO_2:ySiO_2:zH_2O,$$

wherein M is at least one cation having a valence of n, x is from 0 to 5, y is from 1.0 to 100.0, and z is from 0 to 100. In a preferred embodiment, M is a mixture of protons and alkali metal cations, particularly sodium and potassium, and y is at least 1.0 and ranges up to about 25, preferably up to 10. Depending on the required pore size of the zeolite, the value of y will vary. For pore sizes of about 3–4 Å the value of y will be in the range of 1.0 to 10, preferably 2.5 to 5. For pore sizes of approximately 8 Å the value of y ranges from 2.5 to 25 and preferably from 2.5 to 10.

In case x is 0 the zeolite will be a titanium zeolite, whereas with values of x ranging from 0.05 to 5 the zeolite will be a titanium aluminium zeolite.

The original cations M can be replaced at least in part with other cations by well-known exchange techniques. Preferred replacing cations include hydrogen, ammonium, rare earth and mixtures thereof.

Commercially available titanium and titanium aluminium zeolites useful in the present invention, are for example the Engelhard Corporation zeolites ETS-4, ETS-10 and ETAS-10. The ETS series are titanium zeolites and the ETAS material is a titanium aluminium zeolite.

The amount of active metal in the catalyst will also depend on the type of catalyst and the actual reaction. Generally the amount of metal will range from 1 to 60 wt. % based upon the catalyst, preferably 5 to 40 wt. %. The reaction itself requires at least 0.001 wt. %, based upon the weight of the reactants, of the active metal. A preferred range for the amount of active metal in the reaction ranges from 0.01 to 10 wt. %, also calculated on the weight of the reactants.

Various applications of this invention are illustrated in the following examples. For comparing the activities and selectivities of the different catalysts in the methanolysis of triglycerides, the following definitions are used in the data presented below.

The splitting degree is defined as the relative amount of triglycerides that is converted during the reaction:

triglyceride$_{in}$ (wt %)−triglyceride$_{out}$ (wt %)

where triglyceridein (wt %)=100.

The selectivity to fatty acid methylesters is defined as the percentage of methylesters in the product, based on the total amount of product:

$$\frac{C_N\text{-methylesters}_{out}\ (\%)}{\text{methylesters}_{out}\ (\%) + \text{Others}_{out}\ (\%)} * 100\%,$$

where "Others" represent a group, mainly consisting of mono- and diglycerides, which are the regular reaction intermediates, and N is the number of C atoms in the alkylchain of the intended methylester.

The yield (%) is defined as the splitting degree of the triglycerides multiplied by the selectivity to the fatty acid methyl esters.

EXAMPLE 1

A high pressure autoclave was loaded with 110 grams of soybean oil and 0.367 grams of an ETAS-10 zeolite (titanium content: 10.4 wt. %). The autoclave was flushed with nitrogen, evacuated to vacuum and subsequently heated to 220° C., while stirring. A separate bomb, connected to the autoclave, was loaded with 73.6 grams of methanol and also heated to 220° C. When both vessels reached 220° C., a valve was opened between these vessels, and large part of the methanol was pressed by its vapour pressure into the vacuum autoclave. The actual amount of methanol that was transferred to the autoclave was determined by weighting the bomb before and after opening the valve. At the moment of methanol addition, a temperature drop was observed of approximately 60° C., caused by evaporation of the methanol. Simultaneously, the pressure in the autoclave increased to a maximum, which depended on the activity of the catalyst. For this particular experiment, a methanol/soybean oil ratio of 4.5 was obtained, and a maximum pressure of 21 bar.

Samples were taken after different reaction times. The samples were dissolved in heptane and their compositions were determined by gaschromatographic analysis.

After 90 minutes of reaction, a splitting degree of 72.1% was reached, and a selectivity to fatty acid methylesters of 80.0%, resulting in a yield of 57.7% of methylesters.

EXAMPLES 2 TO 4

A series of experiments has been performed according to the procedure described in example 1 using other catalysts. (ETS-4 titanium content: 14.9 wt. %; TIS titanium content: 38 wt. %) The relevant parameters and the activities of the different catalysts are presented in table 1.

TABLE 1

Performance of different catalysts in the alcoholysis of soybean oil with methanol (0.23 wt % of catalyst, based on total autoclave content).

| Exp. | Catalyst | $P_{max}$ (bar) | MeOH/SBO ratio | Splitting (%) | Sel. (%) | Yield (%) |
|---|---|---|---|---|---|---|
| 2 | ETS-10 | 21.0 | 4.2 | 69.0 | 76.2 | 52.6 |
| 3 | ETS-4 | 18.0 | 4.3 | 96.9 | 88.4 | 85.7 |
| 4 | TIS* | 19.0 | 4.1 | 81.7 | 82.1 | 67.1 |

*: Amorphous precipitated titanium silicate

EXAMPLES 5 TO 7

A series of experiments has been performed according to the procedure described in example 1, using tallow instead of soybean oil as feedstock. The results of these experiments are presented in table 2. Titanium content ETAS-10: 9.4 wt. %.

TABLE 2

Performance of different catalysts in the alcoholysis of tallow with methanol (0.23 wt % of catalyst, based on total autoclave content).

| Exp. | Catalyst | $P_{max}$ (bar) | MeOH/tallow ratio | Splitting (%) | Sel. (%) | Yield (%) |
|---|---|---|---|---|---|---|
| 5 | ETAS-10 | 18.5 | 4.3 | 30.6 | 62.4 | 19.1 |
| 6 | ETS-4 | 20.0 | 4.1 | 44.1 | 67.2 | 29.6 |
| 7 | TIS | 17.5 | 4.4 | 34.7 | 56.1 | 19.5 |

EXAMPLES 8 TO 11

Extrudates (1/16", quadrulobes) were prepared from the powdered zeolite materials by mixing the powders with 20 wt. % Versal 250 alumina, as binder, and extruding these mixtures. Extrudates of TIS (1/16", trilobes) were prepared by extruding TIS powder with 20 wt. % Ludox AS-40 (colloidal silica) as binder. A tube reactor was loaded with 150 ml of these extrudates, homogeneously mixed with 150 ml of inert alumina tablets. The tube reactor was heated to various temperatures, and a mixture of soybean oil (LHSV 0.53 h$^{-1}$) and methanol (LHSV 0.29 h$^{-1}$) were pumped over the catalyst. During the run, the pressure was held at 40 bar with nitrogen. Important parameters during these experiments were the splitting degree, the selectivity and the yield to fatty acid methyl esters, achieved under certain conditions. The results of these experiments, using different catalysts, are presented in table 3. For comparison also the conversion over TiO$_2$ (1/8" tablets) is given

TABLE 3

Performance of the solid catalysts in the fixed bed alcoholysis of soybean oil.

| Exp. | Catalyst | Temp. (°C.) | Splitting (%) | Sel. (%) | Yield (%) |
|---|---|---|---|---|---|
| 8 | TiO$_2$* | 220 | 49 | 76 | 37 |
| 9 | ETAS-10 | 220 | 97 | 90 | 87 |
| 10 | ETS-4 | 210 | 94 | 86 | 81 |
| 11 | TIS | 210 | 93 | 90 | 84 |

*: Comparison

EXAMPLES 12 AND 13

Some experiments have been performed according to the procedure described in example 1, but after addition of 3.5 wt % of free fatty acids in the soybean oil feedstock. The results of these experiments are presented in table 4.

TABLE 4

Performance of the solid catalysts in the fixed bed alcoholysis of soybean oil, in the presence of 3.5 wt % free fatty acids.

| Ex | Catalyst | Temp. (°C.) | Splitting (%) | Sel. (%) | Yield (%) |
|---|---|---|---|---|---|
| 12 | ETS-4 | 210 | 91 | 85 | 77 |
| 13 | TIS | 210 | 93 | 90 | 84 |

EXAMPLE 14

A high pressure autoclave was loaded with 200 g of rapeseed oil, 156 g of 2-ethylhexanol and 0.7 g ETS-4. The autoclave was flushed with nitrogen and subsequently heated to 240° C. This temperature was reached after 23 min ($t_0$).

In this experiment the molar ratio of rapeseed oil to 2-ethylhexanol was 5 to 1, and the maximum pressure in the reactor amounted to 3 bar.

Samples were taken at various moments during the reaction and the composition thereof was determined by gas chromatography. After 90 min of reaction at 240° C. the amount of ester in the reaction mixture was 70.2 wt. %, while the ratio of ester formed to the total of products formed was 89%.

The results obtained for the reaction are given in table 5.

TABLE 5

| Time (min) | $T_{amb}$ 0 | 240° 0 | 5 | 10 | 20 | 30 | 50 | 70 | 90 |
|---|---|---|---|---|---|---|---|---|---|
| fatty acid | | | | | | | | | |
| ester of EH | 0 | 0 | 0.5 | 1.7 | 6.9 | 25.0 | 57.5 | 65.0 | 70.2 |
| triglyceride | 56.1 | 54.4 | 54.0 | 52.0 | 44.9 | 26.7 | 2.2 | 0.6 | 0.3 |
| Diglyceride | 0 | 2.7 | 2.7 | 4.0 | 7.1 | 11.4 | 9.0 | 6.0 | 4.2 |
| Monoglyceride | 0 | 0 | 0 | 0 | 0.4 | 1.8 | 6.2 | 5.4 | 4.1 |
| Free fatty acid | 0.1 | 0.1 | 0.11 | 0.13 | 0.15 | 0.12 | 0.12 | 0.14 | 0.13 |
| EH | 43.8 | 42.8 | 42.7 | 42.2 | 40.6 | 35.0 | 25.0 | 22.9 | 21.1 |

EH: 2-ethylhexanol

EXAMPLE 15

A high pressure autoclave was loaded with 280 g of rapeseed oil, 72 g of methanol and 0.7 g ETS-4. The autoclave was flushed with nitrogen and subsequently heated to 230° C. This temperature was reached after 31 min ($t_0$).

In this experiment the molar ratio of rapeseed oil to methanol was 7 to 1, and the maximum pressure in the reactor amounted to 32 bar.

Samples were taken at various moments during the reaction and the composition thereof was determined by gas chromatography. After 90 min of reaction at 230° C. the amount of ester in the reaction mixture was 80.7 wt. %, while the ratio of ester formed to the total of products formed was 93%.

The results obtained for the reaction are given in table 6.

TABLE 6

| Time (min) | 0 T_amb | 0 240° | 5 | 10 | 20 | 30 | 50 | 70 | 90 |
|---|---|---|---|---|---|---|---|---|---|
| Fatty acid | | | | | | | | | |
| ester of MeOH | 0 | 17.0 | 50.8 | 62.1 | 71.6 | 76.6 | 78.4 | 78.9 | 80.7 |
| Triglyceride | 79.5 | 54.2 | 16.5 | 7.4 | 1.8 | 0.6 | 0.2 | 0 | 0 |
| Diglyceride | 0 | 8.0 | 11.4 | 8.9 | 4.2 | 2.3 | 1.3 | 1.0 | 0.8 |
| Monoglyceride | 0 | 2.0 | 5.7 | 7.6 | 8.5 | 7.0 | 6.9 | 6.9 | 5.4 |
| Methanol | 20.5 | 18.8 | 15.6 | 14.0 | 13.9 | 13.5 | 13.2 | 13.2 | 13.1 |

EXAMPLE 16

In a reactor 5 g polyvinylacetate (PVAc, saponification value 650 mg KOH/g) was mixed with 111 g methanol. The reactor was flushed with nitrogen. After heating the mixture to 66° C., 2.3 g of ETS-4 were added under continuous stirring. The reaction of the PVAc to polyvinylalcohol was followed by measuring the saponification value as a function of time. After 4 hours of reaction the saponifacation value was 7.1 mg KOH/g, indicating a high conversion of PVAc to polyvinylalcohol, which was confirmed by HPLC.

EXAMPLE 17

In a reactor 5 g polyvinylacetate (PVAc, saponification value 650 mg KOH/g) was mixed with 111 g methanol. The reactor was flushed with nitrogen. After heating the mixture to 66° C., 2.4 g of ETS-10 were added under continuous stirring. After 4 hours of reaction the saponification value was decreased to 195 mg KOH/g, indicating a hydrolysis degree of PVAc to polyvinylalcohol of more than 60%.

We claim:

1. Process for the transesterification of carboxylic acid esters with an alkanol, a carboxylic acid or a carboxylic acid ester, in which process a catalyst is used which is substantially insoluble in the reaction mixture under reaction conditions, said catalyst comprising at least one silicate of the Group IVB elements of the Periodic Table as the active component.

2. Process according to claim 1, wherein the said Group IVB element is titanium or zirconium.

3. Process according to claim 2, wherein the said catalyst is selected from the group consisting of crystalline titanium silicate, crystalline titanium-aluminium silicate and amorphous titanium silicate.

4. Process according to claim 1, wherein as catalyst a titanium based zeolite is used.

5. Process according to claim 3, wherein said amorphous titanium silicate comprises a homogeneous mixed oxide of silicon and titanium.

6. Process according to claim 1, wherein triglycerides are transesterified with alkanol.

7. Process according to claim 1, wherein an ester or a polymer ester is transesterified.

8. Process according to claim 1, wherein a catalyst is used containing 1 to 60 wt. % of said Group IVB element, calculated as metal.

9. Process according to claim 1, wherein the amount of said Group IVB element, calculated as metal, is at least 0.001 wt. %, based upon the weight of the reactants.

10. Process according to claim 2, wherein the said Group IVB element is titanium.

11. Process according to claim 6, wherein triglycerides are transesterified with methanol.

12. Process according to claim 7, wherein said polymeric ester is polyvinyl acetate.

13. Process according to claim 8, wherein said catalyst contains 5 to 40 wt. % of said Group IVB element, calculated as metal.

14. Process according to claim 9, wherein the amount of said Group IVB element, calculated as metal, is 0.01 to 10 wt. %, based upon the weight of the reactants.

* * * * *

UNITED STATES PATENT AND TRADEMARK OFFICE
CERTIFICATE OF CORRECTION

PATENT NO. : 5,508,457
DATED : April 16, 1996
INVENTOR(S) : Bayense et al.

It is certified that error appears in the above-identified patent and that said Letters Patent is hereby corrected as shown below:

Column 3, line 64, "triglyceridein", should read --triglyceride$_{in}$--.

Signed and Sealed this

Twenty-ninth Day of September, 1998

Attest:

BRUCE LEHMAN

Attesting Officer

Commissioner of Patents and Trademarks